(12) United States Patent
Gaboriault (10) Patent No.: US 11,420,094 B2
(45) Date of Patent: Aug. 23, 2022

(54) TRAINING DEVICE FOR CHEWING AND SWALLOWING

(71) Applicant: Cheryl Gaboriault, Sandwich, MA (US)

(72) Inventor: Cheryl Gaboriault, Sandwich, MA (US)

(*) Notice: Subject to any disclaimer, the term of this patent is extended or adjusted under 35 U.S.C. 154(b) by 97 days.

(21) Appl. No.: 16/905,317

(22) Filed: Jun. 18, 2020

(65) Prior Publication Data
US 2021/0178223 A1    Jun. 17, 2021

Related U.S. Application Data

(60) Provisional application No. 62/974,557, filed on Dec. 11, 2019.

(51) Int. Cl.
*A63B 23/03*    (2006.01)

(52) U.S. Cl.
CPC ........ *A63B 23/032* (2013.01); *A63B 2209/00* (2013.01)

(58) Field of Classification Search
CPC ........................... A63B 23/032; A63B 2209/00
USPC ............................................ 30/414; 604/514
See application file for complete search history.

(56) References Cited

U.S. PATENT DOCUMENTS

| | | | | |
|---|---|---|---|---|
| 2,824,561 A * | 2/1958 | Mueller | ................ | A61J 7/0053 215/11.1 |
| 4,391,391 A * | 7/1983 | Robaldo | ............... | B05C 17/002 222/478 |
| 4,850,968 A * | 7/1989 | Romano | ............. | A61M 5/3243 604/110 |
| 5,259,840 A * | 11/1993 | Boris | .................. | A61M 5/3213 604/218 |
| 5,263,976 A | 11/1993 | Williams | | |
| 5,366,481 A * | 11/1994 | Zade | ..................... | A61J 17/001 606/236 |
| 5,735,772 A | 4/1998 | Schiavoni | | |
| 5,908,440 A * | 6/1999 | McCloskey | ............. | A61J 17/02 606/234 |
| 8,172,725 B2 | 5/2012 | Boutenko et al. | | |
| 9,301,904 B2 * | 4/2016 | Paxson | .................. | A61J 17/02 |
| 9,730,861 B2 | 8/2017 | Lo | | |
| 9,757,616 B2 | 9/2017 | Kwan tai | | |
| D838,368 S | 1/2019 | Rifani | | |
| 2008/0300575 A1 * | 12/2008 | Cleator | ................. | A61M 31/00 604/514 |
| 2009/0182308 A1 * | 7/2009 | Hagbi | .................. | A61J 7/0053 604/514 |
| 2009/0192547 A1 | 7/2009 | Gates | | |

(Continued)

*Primary Examiner* — Nyca T Nguyen
(74) *Attorney, Agent, or Firm* — Nath, Goldberg & Meyer; Richard C. Litman (57) ABSTRACT

The training device for chewing and swallowing can be used by patients who have difficulty chewing and/or swallowing to assist them to learn how to chew and swallow. The device includes a bolus delivery cylinder and a plunger. The bolus delivery cylinder can include a cylindrical housing having a peripheral wall and a hollow interior. The plunger can be slidably received in the cylindrical housing and secured thereto. In some embodiments the peripheral wall can be perforated. The interior of the housing is configured to accommodate small pieces of food. The bolus delivery cylinder can be made from a transparent, flexible material, such as silicon.

17 Claims, 5 Drawing Sheets

(56) References Cited

U.S. PATENT DOCUMENTS

| | | | |
|---|---|---|---|
| 2010/0010471 A1* | 1/2010 | Ladd | A61M 31/007 |
| | | | 604/514 |
| 2010/0063473 A1* | 3/2010 | Schwarz | A61J 7/0053 |
| | | | 604/514 |
| 2010/0211007 A1* | 8/2010 | Lesch, Jr. | A61M 25/1018 |
| | | | 604/97.02 |
| 2010/0230372 A1* | 9/2010 | Lo | A61J 9/08 |
| | | | 215/11.1 |
| 2012/0022446 A1* | 1/2012 | Desai | A61J 7/0053 |
| | | | 604/77 |
| 2012/0066911 A1* | 3/2012 | Hicks | A47G 21/04 |
| | | | 30/141 |
| 2012/0232524 A1* | 9/2012 | Hyun | A61M 5/385 |
| | | | 604/514 |
| 2013/0102997 A1* | 4/2013 | Abbassmovahedi | A61J 17/001 |
| | | | 604/514 |
| 2013/0338639 A1* | 12/2013 | Karpen | A61M 3/0279 |
| | | | 604/514 |
| 2014/0074165 A1* | 3/2014 | Paxson | A61J 17/02 |
| | | | 606/235 |
| 2014/0296868 A1* | 10/2014 | Garrison | A61M 5/3137 |
| | | | 606/127 |
| 2014/0296915 A1* | 10/2014 | Finney | A61J 7/0053 |
| | | | 606/236 |
| 2015/0164736 A1* | 6/2015 | Gallant | A61M 31/00 |
| | | | 600/38 |
| 2016/0360908 A1* | 12/2016 | Naraine | A61J 7/0053 |
| 2019/0307638 A1 | 10/2019 | Martin et al. | |

* cited by examiner

TRAINING DEVICE FOR CHEWING AND SWALLOWING

CROSS-REFERENCE TO RELATED APPLICATION

This application claims the benefit of U.S. Provisional Patent Application No. 62/974,557, filed on 11 Dec. 2019.

BACKGROUND

1. Field

The disclosure of the present patent application relates to oral therapeutic devices, and particularly, to a training device for chewing and swallowing.

2. Description of the Related Art

Patients with feeding and/or swallowing dysfunction have a sensory, motor, oral or other dysfunction that can prevent them from receiving adequate nutrition. Many of these patients often endure aspiration, choking, gagging, vomiting, and starving and may require feeding tubes (gastrostomy tube) to avoid the complications associated with oral ingestion of food.

Learning to chew and swallow can be dangerous and anxiety-provoking for many patients and their families. Feeding and swallowing therapy can be costly and takes months or even years to be effective. Many prior art chewing and swallowing training devices do not release food into the mouth in a progressive, controlled manner and, as such, can increase the chances of choking. Some prior art devices can help a patient to learn chewing skills but are not conducive for teaching swallowing skills as such devices are not designed to accommodate food.

Thus, a training device for chewing and swallowing solving the aforementioned problems is desired.

SUMMARY

The training device for chewing and swallowing can be used by patients who have difficulty chewing and/or swallowing (dysphagia) to assist them to learn how to chew and swallow. The device includes a bolus delivery cylinder and a plunger. The bolus delivery cylinder can include a cylindrical housing having a peripheral wall and a hollow interior. In some embodiments the peripheral wall can be perforated. The interior of the housing is configured to accommodate small pieces of food. The bolus delivery cylinder can be made from a transparent, flexible material, such as silicon. The plunger can be slidably received in the cylindrical housing. The plunger can be made from a material that is stiffer than the bolus delivery cylinder, e.g., polypropylene or other plastic. A twist and lock mechanism can secure the plunger to the cylinder.

In use, small pieces of food can be inserted into the bolus delivery cylinder. The plunger can then be inserted into the bolus delivery cylinder and the training device can be inserted into the patient's mouth. The device is a specialized therapeutic chewing and swallowing tool that gradually allows therapeutic amounts of food to enter the mouth, thereby stimulating and exercising a patient's oral cavity (lips, tongue, and jaw). The holes in the perforated cylinder can allow food particles to be released into the mouth as the patient chews on the cylinder. The silicone material of the cylinders provides a soft surface for the patient to practice chewing, while the food dispensing cylinder provides small portions of food that is needed to learn bolus control (food in the mouth) and the development of nutritive chewing for functional eating and swallowing skills. Thus, the device gradually and safely aids in the development of safe and effective chewing and side biting skills, as well as lateral and rotary tongue motion in the oral phase of eating and swallowing.

A training kit for chewing and swallowing can include a plurality of bolus delivery cylinders. The kit can include at least one solid cylinder (sham bolus) with no holes, one or more perforated cylinders, and optionally at least one scrub brush for cleaning. The perforated cylinders can have the same number or a different number of food delivery holes. The holes allow food to be released into the mouth when a patient chews on the cylinder. As a patient advances to higher levels of therapy, cylinders with increasing numbers of holes may be used to progressively allow more food to be released.

A therapist using the kit may first select a level 1 sham bolus and progress through the levels (2-N) of cylinders with increasing number of holes, as is deemed appropriate for each individual patient. This provides the patient with gradual food-based therapeutic exercises, while limiting the risk of aspiration, particularly under medical professional supervision and guidance in skilled dysphagia therapy. In addition to clinical use, the device is safe for home practice. Home environment eating practice sessions are essential for best patient outcomes and quality of life, but due to the risk of airway compromise and choking, home feeding practice is preferably guided by a clinician. The device supports independent, self-feeding skills, as most patients can hold the device while eating food. In addition the device provides improved quality of life for patients by allowing them to experience foods for pleasure, such as birthday cake or their favorite foods.

In addition, advances made by a patient using the device can be easily monitored and measured based on the patient's progression through the cylinder levels (1-N) for maximum, safe improvements in chewing and swallowing results. Monitoring a patient's progress in this manner can be important for medical insurance documentation. The device can be used by a number of professionals, including but not limited to: feeding specialists; physicians; nurses; speech therapists; occupational therapists; autism specialists; caregivers; nurses; teachers; and dietitians.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
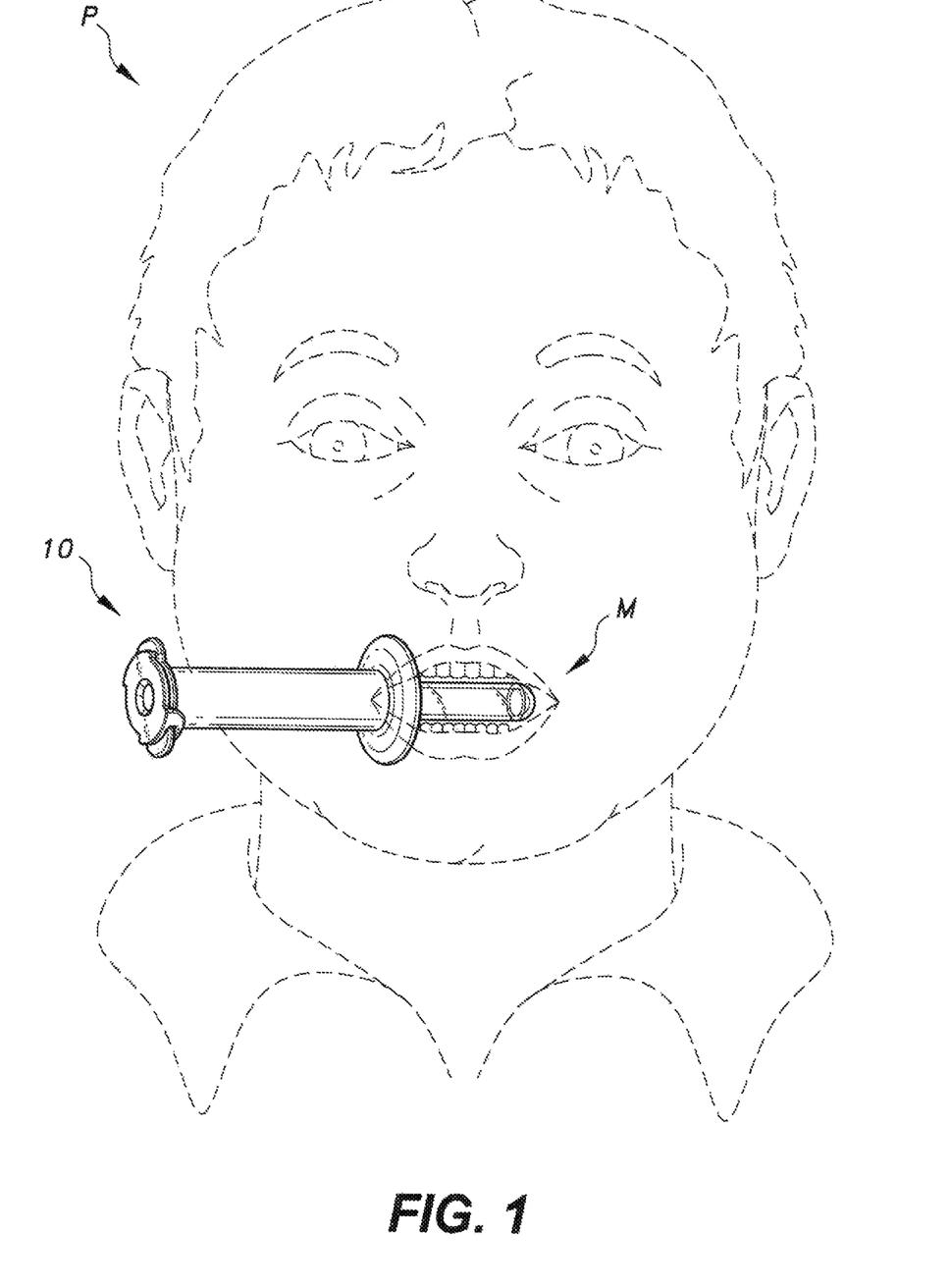
FIG. 1 is an environmental, perspective view of a training device for chewing and swallowing, being used by a patient.
Figures 2, 3:
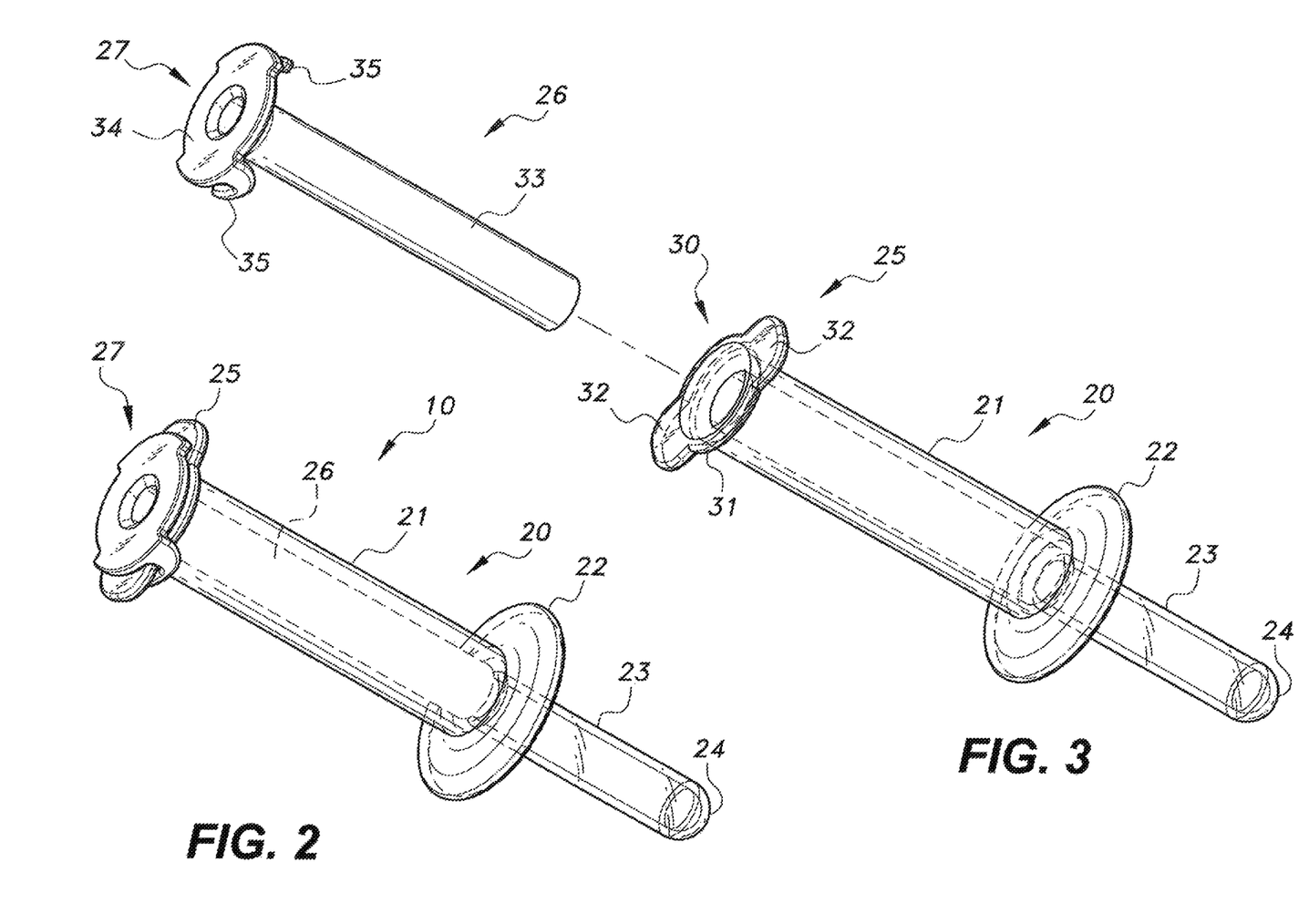
FIG. 2 is a perspective view of the training device for chewing and swallowing of FIG. 1.
FIG. 3 is an exploded, perspective view of the training device for chewing and swallowing of FIG. 1.

FIG. 1 shows the training device for chewing and swallowing 10 positioned in the mouth M of a patient P. The training device 10 can be administered to the patient with the assistance of a doctor, technician, parent or caregiver, to assist the patient with chewing and swallowing. FIGS. 2-3 show the details of the training device for chewing and swallowing 10. The device 10 can include a bolus delivery cylinder 20; and a plunger 26. The bolus delivery cylinder 20 can include a cylindrical housing having a peripheral wall and a hollow interior. In some embodiments the peripheral wall can be perforated or include a plurality of holes. The housing can be configured to accommodate small pieces of food therein. The bolus delivery cylinder 20 can be made of a flexible, transparent silicon to provide flexibility and visibility of the contents (if any) of the bolus delivery cylinder 20, as described further below. The plunger 26 can be made from a stiffer material than the bolus delivery cylinder 20, e.g., polypropylene. In an embodiment, the polypropylene may be treated to be opaque or transparent, or may be tinted in various colors.

The bolus delivery cylinder 20 includes a cylindrical handle portion 21 adjacent an open proximate end 30 and a cylindrical chewing member 23 at a closed distal end 24. A circular shield flange 22 separates the handle portion 21 from the chewing member 23. As can best be seen in FIGS. 2-3, the cylindrical handle portion 21 has a larger external diameter than an external diameter of the cylindrical chewing member 23. With this configuration, only the chewing member 23 of the bolus delivery cylinder 20 can be inserted into the patient's mouth. A plunger lock mechanism 25 extends from the proximate end 30. The plunger lock mechanism 25 includes a circular plate 31 and radially extending receiving tabs 32 extending from opposite sides of the plate 31.

The plunger 26 includes a cylindrical body 33 having a flat distal end, an opposing proximate end, and a cylinder lock mechanism 27 extending from the proximate end. The cylindrical body 33 has an exterior surface with a diameter that is sized and configured to closely engage, e.g., slidably engage, the inner walls of the cylindrical handle portion 21, similar to a syringe. The cylinder lock mechanism 27 includes a plate 34 with locking hooks 35 extending axially from opposite sides of the plate 34. One end of the locking hooks 35 can extend 90 degrees from the plate bend and an opposing end can of the locking hooks 35 can curve inward. To lock the plunger 26 to the cylinder 20, the cylindrical body is first inserted into the cylinder 20, while keeping the locking hooks 35 in between the tabs 32, as shown in FIG. 3. Then, the plunger 26 is rotated clockwise relative to the cylinder 20 until the locking hooks 35 engage the tabs 32, as shown in FIG. 2.

As noted above, the training device for chewing and swallowing 10 may be provided in the form of a kit. FIGS. 4A-4D show examples of four bolus delivery cylinders that may be included in the kit, along with the plunger 26 as shown in FIGS. 2-3. While four examples of bolus delivery cylinders are shown, it should be understood that a kit may include more or less cylinders.

A first example of a bolus delivery cylinder 20 is shown in FIGS. 2-4A. The shield flange 22 can include a frusto-conical upper surface 40 that extends from the handle portion 21 to the outer circular edge of the shield flange 22. The silicon material of the shield flange 22 provides a soft and pliable barrier to limit the extent the device 10 can be inserted into a patient's mouth. As is shown in FIGS. 2-4A, the chewing member 23 is a cylindrical member with a rounded closed tip 24 and a solid sidewall 44. The bolus delivery cylinder 20 can be considered a sham bolus, meaning it is not intended to dispense food, but rather provides the feel of a small amount of food (bolus) trapped within the chewing member 23, for chewing therapy. This cylinder 20 is useful for supervised use by patients who are not permitted to eat food due to medical complications. The patient can see and feel the food inside the chewing member 23 during chewing practice in dysphagia therapy. No food flavor or fragments can enter the mouth, as the interior of the chewing member 23 is completely sealed by plunger 26 to form a closed sealed chamber. Under professional supervision in dysphagia therapy, the benefits of using the "sham bolus" cylinder 20 include, but are not limited to: developing pre-feeding oral motor and swallowing skills; increasing visual sensory processing information of specific foods and how and to what extent the food is altered as they chew on it over time; increasing tactile sensory processing about the feel of food on the molar surfaces while masticating; improving auditory sensory information relating to mastication of food; and increasing saliva management for swallowing oral secretions while chewing on food without the risk of aspiration on food particles.

Figure 4A:
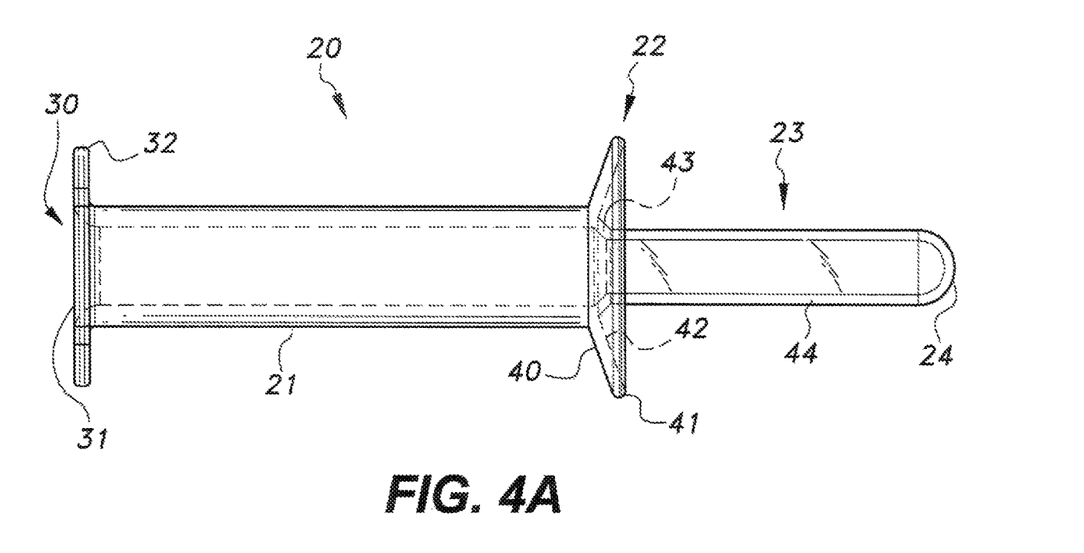
FIG. 4A is a side view of a first silicone bolus delivery cylinder of the training device for chewing and swallowing of FIG. 1.
Figure 4B:
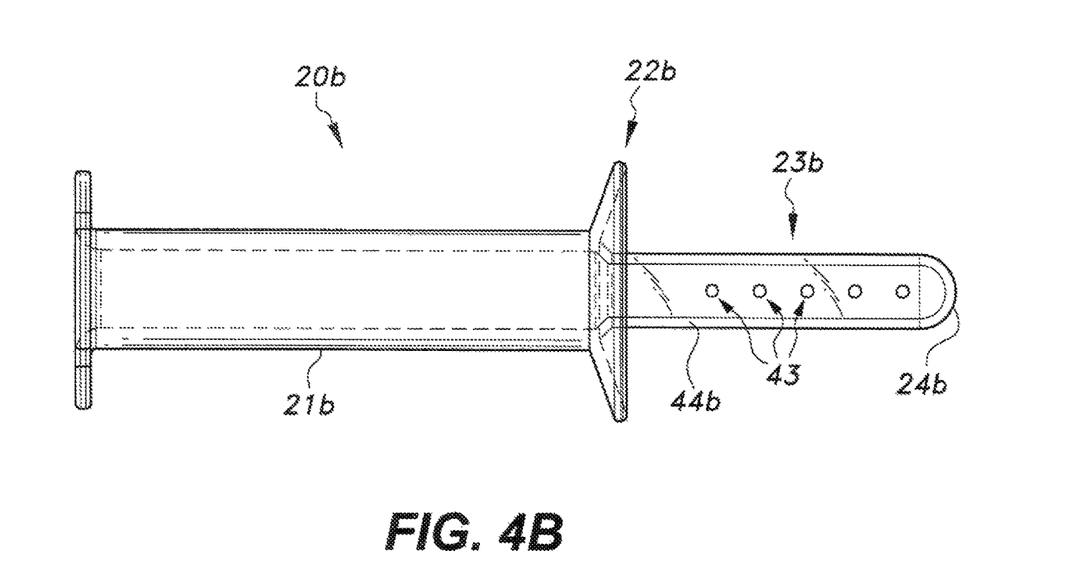
FIG. 4B is a side view of a second silicone bolus delivery cylinder of the training device for chewing and swallowing of FIG. 1.

A second example of a bolus delivery cylinder 20b is shown in FIG. 4B. This bolus delivery cylinder 20b is similar to cylinder 20, except that cylinder 20b includes a perforated peripheral wall 44b with holes 43 to allow a limited amount of flavor and food particles to enter the mouth. In the embodiment shown, five (5) holes 43 extend through the peripheral wall 44b of the chewing member 23b, and are arranged in a linear fashion along one side of the chewing member 23b. It should be understood that the number of holes 43 can be more or less than five depending on the size of the holes and the patient's needs. The holes 43 allow limited food particles to enter into the mouth as the patient chews on the cylinder. The benefits of chewing on the bolus delivery cylinder 20b include, but are not limited to improving the frequency and timing of swallowing, improving oral sensory skills via controlled, gradual release of food particles with flavor and texture into the mouth, improving saliva control and swallowing given gradual increase in food stimulation in the mouth, increasing tongue and oral motor skills by gradually introducing flavor and food particles into the mouth, improving muscular control for chewing with mandibular jaw action for moving foods in the mouth to form a gradual bolus for swallow activation, and developing independent, self-feeding as the patient learns to hold the device 10 while chewing therapeutic food. Advancement to cylinders with a larger number of holes can be determined by a medical assessment of safe oral and swallowing skills.

Figure 4C:
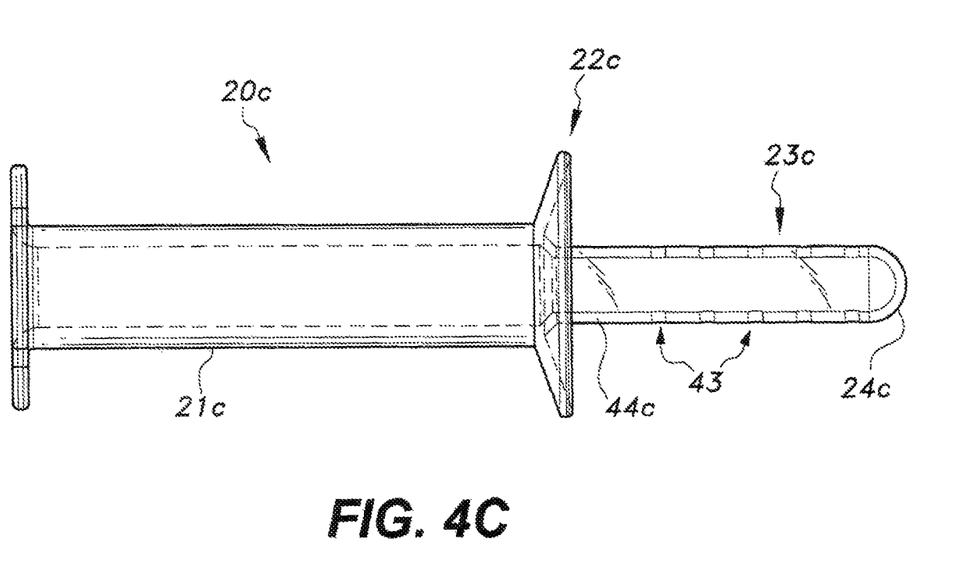
FIG. 4C is a side view of a third silicone bolus delivery cylinder of the training device for chewing and swallowing of FIG. 1.

A third example of a bolus delivery cylinder 20c is shown in FIG. 2C. This bolus delivery cylinder 20c is similar to cylinder 20b, but includes more holes in the perforated peripheral wall 44c to allow more food particles to enter the mouth. In the embodiment shown in FIG. 2C, the peripheral wall 44c of the chewing member has ten (10) holes defined therethrough. It should be understood that the number of holes 43 can be more or less than ten depending on, e.g., the size of the holes and the patient's needs. Small food particles can flow through the holes 43 into the mouth as the patient chews on the cylinder 20. The benefits of chewing on the bolus delivery cylinder 20c include, but are not limited to, improving the frequency and timing of swallowing, improving oral sensory skills via controlled, gradual release of food particles with flavor and texture into the mouth, improving saliva control and swallowing given gradual increase in food stimulation in the mouth, increasing tongue and oral motor skills by gradually introducing flavor and food particles into the mouth, improving muscular control for chewing with mandibular jaw action for moving foods in the mouth to form a gradual bolus for swallow activation, and increasing bolus control and swallowing effectiveness as the amount of food is allowed into the mouth via patient mastication. Advancing to the next cylinder level can be determined by a medical assessment of safe oral and swallowing skills.

Figure 4D:
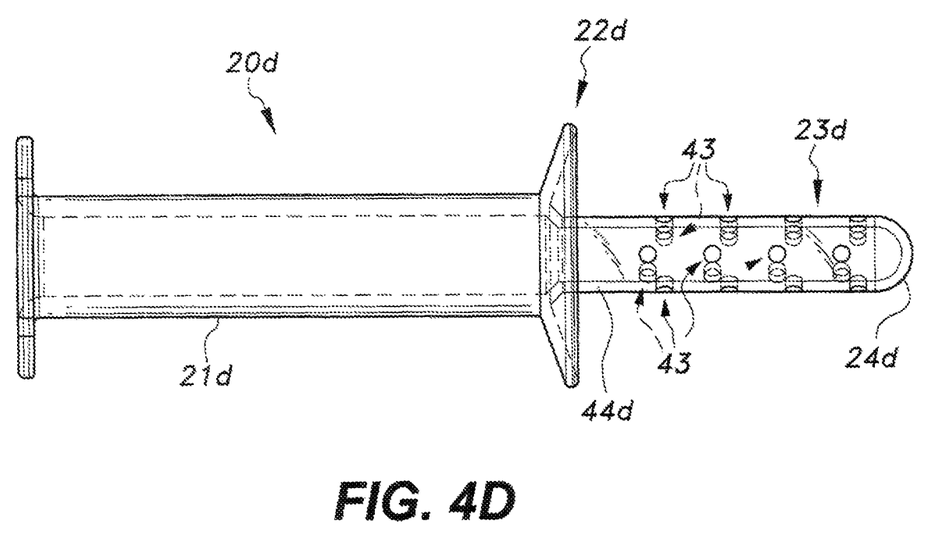
FIG. 4D is a side view of a fourth silicone bolus delivery cylinder of the training device for chewing and swallowing of FIG. 1.

A fourth example of a bolus delivery cylinder 20d is shown in FIG. 2D. This bolus delivery cylinder 20d is similar to cylinder 20c, but is specially designed to allow an even greater, but still metered amount of food to flow into the mouth as the patient chews on the cylinder. The bolus delivery cylinder 20d has an increased number of holes 43, e.g., at least 15 holes, that extend through the sidewall 44d of the chewing member 23d, to allow the patient or therapist to guide intake of a greater increased amount of food (maximum food intake is 20 ml). It should be understood that the number of holes 43 can be determined by the size of the holes, the strength of the silicone material, and the overall size of the device 10. The benefits of chewing on the bolus delivery cylinder 20d include, but are not limited to, improving the frequency and timing of swallowing, improving oral sensory skills via controlled, gradual release of food particles with flavor and texture into the mouth, improving saliva control and swallowing given gradual increase in food stimulation in the mouth, increasing tongue and oral motor skills by gradually increasing the amount of flavor and food particles released into the mouth, improving muscular control for chewing with mandibular jaw action for moving foods in the mouth to form a gradual bolus for swallow activation, and developing independent, self-feeding as the patient learns to hold the device 10 while chewing therapeutic food, and developing safe and effective oral and swallowing skills for patient advancement to strips of soft, solid foods based upon medical professional assessment.

Figure 5:
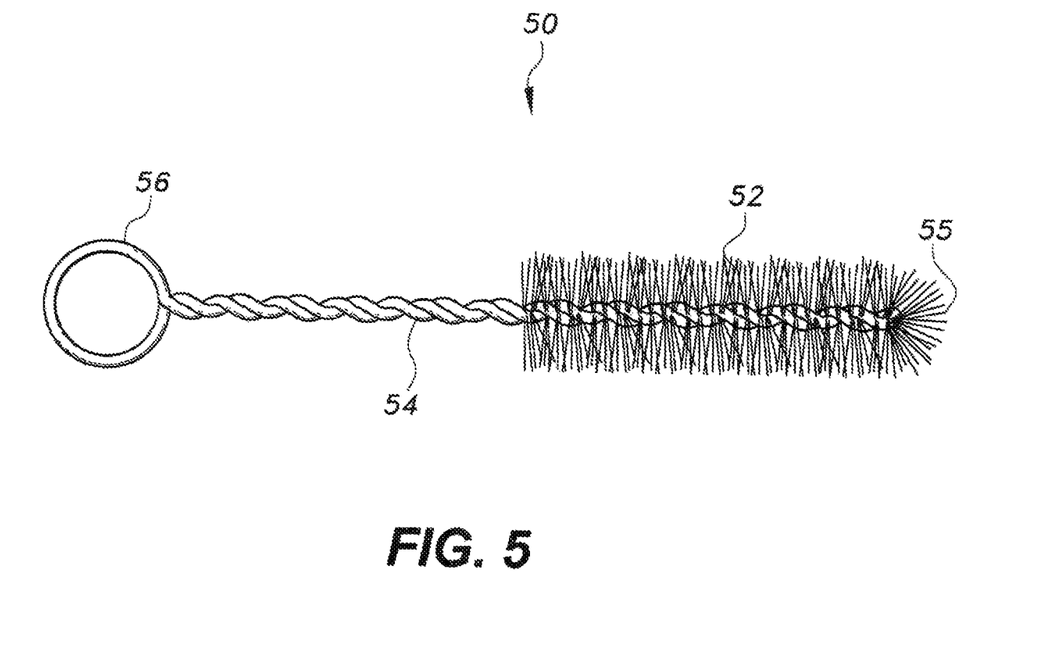
FIG. 5 is a side view of a brush for cleaning the silicone bolus delivery cylinders of the training device for chewing and swallowing of FIG. 1.

As previously noted, the training device for chewing and swallowing 10 may be provided in the form of a kit. The kit may include a plunger 26 and a least one bolus delivery cylinder 20, 20b, 20c, 20d. In addition, the kit may include a cleaning brush. FIG. 5 shows one embodiment of a brush 50 that is useful for cleaning the bolus delivery cylinder(s) 20, 20b, 20c, 20d, provided in the kit. The brush 50 is similar to a test tube brush and includes a plurality of bristles 52 mounted on a twisted wire handle 54, to form a cylindrical outer brush tip surface with a rounded head 55 at a distal end of the brush 50. The twisted wire handle 54 transitions to a wire ring 56 on the proximate end of brush 50. The wire ring 56 may be used to hang the brush 50, when it is not in use, or may provide a finger hook for increased control. The kit can further include instructions for the professional using the device.

A complete professional feeding and swallowing assessment can be conducted to determine the patient's oral-pharyngeal function level and safety for chewing and swallowing prior to offering foods inside the mouth. The training device for chewing and swallowing is preferably for individual use only and not recommended for sharing with other individuals. Professional and caregiver supervision is required for optimal safety when using the device. It is not designed to be used without proper medical professional supervision.

Prior to and after use, the plunger and the bolus delivery cylinder(s) should be thoroughly cleaned using the brush and hot soapy water prior. The training device for chewing and swallowing is top rack dishwasher safe, but drying in the lower rack of the dishwasher should be avoided. The clinician can select the bolus delivery cylinder that supports the patient's level of chewing and swallowing abilities, based upon a feeding-dysphagia assessment. The clinician can then cut the desired food into strips or small pieces and insert into the selected bolus delivery cylinder. Hard or sharp foods such as: granola, nuts, seeds, corn chips, corn nuts, should be avoided as these foods may tear the silicone material of the cylinder. The clinician can then slide the plunger into the cylinder to press food into the chewing member and then twist the plunger to lock the plunger locking hooks to the cylinder tabs to secure the plunger to the bolus delivery cylinder. The clinician can then prompt the patient to look at the food and then position the chewing member onto molar surfaces for chewing practice and feeding-swallowing therapy. In particular, it can be helpful to cue the patient to keep the device positioned on the molar surfaces while providing physical guidance to bite, chew and swallow for skilled dysphagia therapy. The clinician can decide to upgrade to a bolus delivery cylinder with increased holes as appropriate based on a skilled assessment of the patient's oral and pharyngeal abilities and progress through the bolus delivery cylinders as the patient improves chewing, eating and swallowing skills. The patient may progress to other foods and textures under skilled supervision of a feeding-swallowing clinician.

It is to be understood that the training device for chewing and swallowing is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A training device for chewing and swallowing, comprising:
   a cylindrical plunger having a distal end and an opposing proximate end, the proximate end including a plunger lock mechanism; and
   a hollow bolus delivery cylinder configured to slidably receive the cylindrical plunger, the cylinder having a closed distal end, an open proximate end, a cylindrical handle portion and a cylinder lock mechanism adjacent the proximate end, a cylindrical chewing member adjacent the distal end, and a circular shield flange separating the handle portion from the chewing member, wherein
the cylinder lock mechanism is configured to engage the plunger lock mechanism to secure the cylindrical plunger to the hollow bolus delivery chamber; thereby preventing the cylindrical plunger from sliding further into the hollow bolus delivery chamber and preventing the cylindrical plunger from sliding further out of the hollow bolus delivery chamber.

2. The training device for chewing and swallowing as recited in claim 1, wherein the bolus delivery cylinder is made from silicon.

3. The training device for chewing and swallowing as recited in claim 1, wherein:
   the cylinder lock mechanism includes a central plate and locking hooks extending axially from opposite sides of the plate; and
   the plunger lock mechanism includes radially extending receiving tabs;
   whereby the plunger can be rotated within the bolus delivery cylinder until the locking hooks engage the tabs to secure the cylindrical plunger to the hollow bolus delivery cylinder.

4. The training device for chewing and swallowing as recited in claim 1, wherein:
   a peripheral wall of the chewing member is perforated and includes a plurality of holes extending therethrough.

5. The training device for chewing and swallowing as recited in claim 4, wherein the plurality of holes are arranged in a linear array that extends axially along one side of the chewing member.

6. The training device for chewing and swallowing as recited in claim 5, wherein the plurality of holes comprises five holes.

7. The training device for chewing and swallowing as recited in claim 4, wherein the plurality of holes comprises from five to fifteen holes.

8. The training device for chewing and swallowing as recited in claim 1, wherein:
   the handle portion has a first diameter;
   the chewing member has a second diameter;
   the shield flange has an outer circular edge with a third diameter; and
   the first diameter is greater than the second diameter and the third diameter is greater than the first diameter.

9. The training device for chewing and swallowing as recited in claim 1, wherein the shield flange further comprises:
   an upper frustoconical surface that extends from the handle portion to an outer edge of the shield flange.

10. A training kit for chewing and swallowing, comprising:
    a cylindrical plunger having a distal end and an opposing proximate end, the proximate end including a plunger lock mechanism; and
    at least one hollow bolus delivery cylinder configured to slidably receive the cylindrical plunger, the cylinder having a closed distal end, an open proximate end, a cylindrical handle portion with a cylinder lock mechanism adjacent the proximate end, a cylindrical chewing member adjacent the distal end, and a circular shield flange separating the handle portion from the chewing member, wherein
    the cylinder lock mechanism is configured to engage the plunger lock mechanism to secure the cylindrical plunger to the hollow bolus delivery chamber; thereby preventing the cylindrical plunger from sliding further into the at least one hollow bolus delivery chamber and preventing the cylindrical plunger from sliding further out of the at least one hollow bolus delivery chamber.

11. The training kit as recited in claim 10, wherein the at least one bolus delivery cylinder is made from silicon.

12. The training kit as recited in claim 10, wherein
    the at least one bolus delivery cylinder comprises one bolus delivery cylinder;
    the chewing member includes a solid peripheral wall; and
    the plunger and the peripheral wall form a closed, sealed chamber when the plunger is inserted into the handle portion.

13. The training kit as recited in claim 11, wherein
    the at least one bolus delivery cylinder comprises a first bolus delivery cylinder and a second bolus delivery cylinder;
    the chewing member of the first bolus delivery cylinder comprises a solid peripheral wall; and
    the chewing member of the second bolus delivery cylinder comprises a perforated peripheral wall.

14. The training kit as recited in claim 13, wherein the perforated peripheral wall includes a plurality of holes arranged in a linear array that extends axially along one side thereof.

15. The training kit as recited in claim 14, wherein the plurality of holes comprises five holes.

16. The training kit as recited in claim 13, further comprising a third bolus delivery cylinder, wherein:
    the chewing member of the third bolus delivery cylinder includes a perforated peripheral wall having a greater number of holes than the chewing member of the second bolus delivery cylinder.

17. The training kit as recited in claim 16, wherein the chewing member of the second bolus delivery chamber comprises five holes and the chewing member of the third bolus delivery member comprises ten holes.

\* \* \* \* \*